US007485623B2

(12) United States Patent
Bua (10) Patent No.: US 7,485,623 B2
(45) Date of Patent: Feb. 3, 2009

(54) REDUCTION OF BREAST DENSITY WITH 4-HYDROXY TAMOXIFEN

(75) Inventor: Jay Bua, Oakton, VA (US)

(73) Assignee: Laboratoires Besins International SA, Paris (FR)

( * ) Notice: Subject to any disclaimer, the term of this patent is extended or adjusted under 35 U.S.C. 154(b) by 0 days.

(21) Appl. No.: 10/734,644

(22) Filed: Dec. 15, 2003

(65) Prior Publication Data

US 2004/0138314 A1   Jul. 15, 2004

Related U.S. Application Data

(60) Provisional application No. 60/433,958, filed on Dec. 18, 2002.

(51) Int. Cl.
*A61K 31/19* (2006.01)
*A61K 31/195* (2006.01)

(52) U.S. Cl. .................. 514/12; 514/561; 424/449; 424/488

(58) Field of Classification Search ................. 514/651, 514/449, 448, 561; 424/449, 488
See application file for complete search history.

(56) References Cited

U.S. PATENT DOCUMENTS

| 4,919,937 | A | * | 4/1990 | Mauvais-Jarvis et al. .... 424/449 |
|---|---|---|---|---|
| 4,973,755 | A | | 11/1990 | Grafe et al. |
| 5,045,553 | A | * | 9/1991 | Ueda et al. ................. 514/344 |
| 5,613,958 | A | | 3/1997 | Kochinke et al. |
| 5,720,963 | A | | 2/1998 | Smith |
| 5,820,877 | A | * | 10/1998 | Yamaguchi et al. ......... 424/449 |
| 6,013,270 | A | | 1/2000 | Hargraves et al. |
| 6,503,894 | B1 | | 1/2003 | Dudley et al. |
| 2003/0087885 | A1 | | 5/2003 | Masini-Eteve et al. |
| 2004/0086552 | A1 | | 5/2004 | Klokkers et al. |
| 2005/0031695 | A1 | | 2/2005 | Rouanet et al. |
| 2005/0032909 | A1 | | 2/2005 | Lignieres et al. |
| 2005/0032910 | A1 | | 2/2005 | Palumbo et al. |
| 2005/0158388 | A1 | | 7/2005 | Le Nestour et al. |
| 2005/0208139 | A1 | | 9/2005 | Hilt et al. |
| 2005/0209340 | A1 | | 9/2005 | Le Nestour |
| 2006/0105041 | A1 | | 5/2006 | Masini-Eteve |

FOREIGN PATENT DOCUMENTS

| DE | 38 36 862 A1 | 5/1990 |
|---|---|---|
| EP | 513 832 | 11/1992 |
| WO | WO 85/03228 | 8/1985 |
| WO | WO 95/24187 | 9/1995 |

OTHER PUBLICATIONS

Brisson et al. (Cancer Epidemiology, Biomarkers & Prevention 2000; 9: 911-915).*
Pujol et al. (Cancer Chemother. Pharmacol 1995; 36: 493-498).*
Mauvais-Jarvis (Cancer Research 1986; 46: 1521-1525).*
Atkinson et al. (Cancer Epidemiology, Biomarkers & Prevention 1999; 8: 863-866).*
Boyd et al. (J. Nat. Cancer Inst. 1995; 87: 670-675).*
Tan et al. (AAPS PharmSciTech 2000; 1; Article 24).*
Alberti et al. (Journal of Controlled Release 2001; 71: 319-327).*
Kolb et al. (Radiology 2002; 225; 165-175).*
International Search Report.
F. Kuttenn et al., "Pricipe de l'adminstration percutanée des antiestrogènes en pathologie mammaire", Contracept. Fertil. Sex., 1991, vol. 19, No. 2, pp. 165-171.
Catherine Malet et al., "Effect of 4-hydroxytamoxifen isomers on growth and ultrastructural aspects of normal human breast epithelial (HBE) cells in culture", Journal of Steroid Biochemistry and Molecular Biology 82, (2002), pp. 289-296.
Charlotte Atkinson et al., "Mammographic Patterns as a Predictive Biomarker of Breast Cancer Risk: Effect of Tamoxifen", Cancer Epidemiology, Biomarkers & Prevention, vol. 8, Oct. 1999, pp. 863-866.
J. Barrat et al., "Effet in vivo de l'administration locale de progestérone sur l'activité mitotique des galactophores humains", J. Gynecol. Obstet. Biol. Reprod. 19: 269-274 1990.
N.F. Boyd et al., "Relationship Between Mammographic and Histological Risk Factors for Breast Cancer", Journal of the National Cancer Institute. vol. 84, No. 15, Aug. 5, 1992, pp. 1170-1179.
N.F. Boyd et al., "Quantitative Classification of Mammographic Densities and Breast Cancer Risk: Results from the Canadian National Breast Screening Study", Journal of the National Cancer Institute, vol. 87, No. 9, May 3, 1995, pp. 670-675.
Norman F. Boyd et al., "Effects at Two Years of a Low-Fat High-Carbohydrate Diet on Radiologic Features of the Breast: Results from a Randomized Trial", Journal fo the National Cancer Institute, vol. 89, No. 7, Apr. 2, 1997, pp. 488-496.
Jacques Brisson et al., "Tamoxifen and Mammographic Breast Densities", Cancer Epidemiology, Biomarkers & Prevention, vol. 9, Sep. 2000, pp. 911-915.
Celia Byrne, "Studing Mammographic Density: Implications for Understanding Breast Cancer", Journal of the National Cancer Institute, vol. 89, No. 8, Apr. 16, 1997, pp. 531-537.
Philip Carthew et al., "Cumulative exposure to tamoxifen: DNA adducts and liver cancer in the rat", Arch Toxicol (2001) 75: 375-380.
Gerard Chetrite et al., "Effect of Promegestone, Tamoxifen, 4-Hydroxytamoxifen and ICI 164,384 on the Oestrone Sulphatase Activity of Human Breast Cancer Cells", Anticancer Research 13: 931-934 (1993).
Eric C. Dietze et al., "Tamoxifen but Not 4-Hydroxytamoxifen Initiates Apoptosis in p53(-) Normal Human Mammary Epithelial Cells by Inducing Mitochondrial Depolarization", The Journal of Biological Chemistry vol. 276, No. 7, Issue of Feb. 16, 2001, pp. 5384-5394.

(Continued)

*Primary Examiner*—Brandon J Fetterolf
(74) *Attorney, Agent, or Firm*—Foley & Lardner LLP (57) ABSTRACT

A method of treatment comprises administering 4-hydroxy tamoxifen percutaneously to a patient having dense breast tissue. The 4-hydroxy tamoxifen may be formulated in a hydroalcoholic gel or an alcoholic solution.

25 Claims, 1 Drawing Sheet

OTHER PUBLICATIONS

Laurie L. Fajardo MD et al., "Correlation Between Breast Parenchymal Patterns and Mammographers' Certainty of Diagnosis", Investigative Radiology, vol. 23, No. 7,. Jul. 1988, pp. 505-508.

Ian S. Fentiman, "Tamoxifen and Mastalgia an Emerging Indication", Drugs, vol. 32, No. 6, Dec. 1986, pp. 477-480.

I.S. Fentiman et al., "Dosage and duration of tamoxifen treatment for mastalgia: a controlled trial", Br. J. Surg. Sep. 1988, vol. 75, No. 9, pp. 845-846.

I.S. Fentiman et al., "Studies of tamoxifen in women with mastalgia*", The British Journal of Clinical Practice, Supplement 68, vol. 43, No. 11, Nov. 1989, pp. 34-36.

N. Giambiagi et al., "Immunological Differences Between the Estradiol-, Tamxifen- and 4-Hydroxy-Tamoxifen-Estrogen Receptor Complexes Detected by Two Monoclonal Antibodies", J. Steroid Biochem. vol. 30, No. 1-6, pp. 213-217, 1988.

Susan C. Harvey et al., "Marked Regression of a Nonpalpable Breast Cancer After Cessation of Hormone Replacement Therapy", American Journal of Roentgenology, Aug. 1996, 167: 394-395.

Jennifer A. Harvey et al., "Short-term Cessation of Hormone Replacement Therapy and Improvement of Mammographic Specificity", Journal of the National Cancer Institute, vol. 89, No. 21. Nov. 5, 1997, pp. 1623-1625.

IBIS investigators, "First results from the International Breast Cancer Intervention Study (IBIS-I): a randomised prevention trial", The Lancet, vol. 360, Sep. 14, 2002, pp. 817-824.

Susan Jenks, "Dense Breast Tissues May Hold Increased Cancer Risk for Some", Journal of the National Cancer Institute, vol. 86, No. 8, Apr. 20, 1994, pp. 578-580.

V. Craig Jordan et al., "Metabolites of tamoxifen in animals and man: identification, pharmacology, and significance", Breast Cancer Research and Treatment, 2, pp. 123-138, 1982.

Karla Kerlikowske MD et al., "Effect of Age, Breast Density, and Family History on the Sensitivity of First Screening Mammography", JAMA, vol. 276, No. 1, Jul. 3, 1996, pp. 33-38.

Z. Kaufman et al., "The Mammographic Parenchymal Patterns of Women on Hormonal Replacement Therapy", Clinical Radiology (1991), 43, 389-392.

Thomas M. Kolb MD et al., "Comparison of the Performance of Screening Mammography, Physical Examination, and Breast US and Evaluation of Factors that Influence Them: An Analysis of 27,825 Patient Evaluations", Radiology, vol. 225, No. 1, Oct. 2002, pp. 165-175.

George G.J.M. Kuiper et al., "Comparision of the Ligand Binding Specificity and Transcript Tissue Distribution of Estrogen Receptors α and β", Endocrinology, vol. 138, No. 3, 1997, pp. 863-870.

Frédérique Kuttenn et al., "Médecine et Thérapeutique", C.R. Acad. Sc. Paris , , Série III, No. 12, 1985, 300:457-461.

Winnie Leung MD et al., "Mammographic density in women on postmenopausal hormone replacement therapy", Surgery, vol. 122, No. 4, Oct. 1997, pp. 669-674.

L. Ma et al., "Case-Control Study of Factors Associated With Failure to Detect Breast Cancer by Mammography", Journal of the National Cancer Institute, vol. 84, No. 10, May 20, 1992, pp. 781-784.

Catherine Malet et al., "Tamoxifen and Hydroxytamoxifen Isomers versus Estradiol Effects on Normal Human Breast Cells in Culture", Cancer Research, vol. 48, No. 24, Dec. 15, 1988, pp. 7193-7199.

Pierre Mauvais-Jarvis et al., "trans-4-Hydroxytamoxifen Concentration and Metabolism after Local Percutaneous Administration to Human Breast", Cancer Research, vol. 46, Mar. 1986, pp. 1521-1525.

Henri Pujol et al., "Phase I Study of percutaneous 4-hydroxy-tamoxifen with analyses of 4-hydroxy-tamoxifen concentrations in breast cancer and normal breast tissue", Cancer Chemother. Pharmacol., 36:493-498 (1995).

Lawrence H. Block PhD "Epidermal and Transdermal Drug Delivery", The Science and Practice of Pharmacy, Medicated Topicals, pp. 836-857 (2000).

David W. Robertson et al., "Synthesis of the E and Z Isomers of the Antiestrogen Tamoxifen and Its Metabolite, Hdroxytamoxifen, in Tritium-Labeled Form", J. Org. Chem., 1982, vol. 47, No. 12, pp. 2387-2393.

David W. Robertson et al., "Tamoxifen Antiestrogens, a Comparison of the Activity, Pharmacokinetics, and Metabolic Activation of the CIS and Trans Isomers of Tamoxifen" Journal of Steroid Biochemistry, vol. 16, pp. 1-13, (1982).

Carolyn M. Rutter, PhD et al., "Changes in Breast Density Associated With Initiation, Discontinuation. and Continuing Use of Hormone Replacement Therapy", JAMA, vol. 285, No. 2, Jan. 10, 2001, pp. 171-176.

Audrey F. Saftlas et al., Mammographic Parenchymal Patterns and Breast Cancer Risk, Epidemiologic Reviews, vol. 9, 1987, pp. 146-174.

Fabrice Sauvez et al., "Cutaneously applied 4-hydroxytamoxifen is not carcinogenic in female rats", Carcinogenesis vol. 20, No. 5, pp. 843-850 1999.

Hong Ju Son et al., "Significance of Follow-Up Mammography in Estimating the Effect of Tamoxifen in Breast Cancer Patients Who Have Undergone Surgery", American Journal of Roentgenology, 173: 905-909 (1999).

Darcy V. Spicer et al., "Changes in Mammographic Densities Induced by a Hormonal Contraceptive Designed to Reduce Breast Cancer Risk", Journal of the National Cancer Institute, vol. 86, No. 6, Mar. 16, 1994, pp. 431-436.

Giske Ursin et al., The Detection of Changes in Mammographic Densities, Cancer Epidemiology, Biomarkers & Prevention, vol. 7, Jan. 1998, pp. 43-47.

John N. Wolfe MD, "Risk for Breast Cancer Development Determined by Mammographic Parenchymal Pattern", Cancer, May 1976, vol. 37, No. 5, pp. 2486-2492.

Ashini L. Wijayaratne et al., Comparative Analyses of Mechanistic Differences Among Antiestrogens, Endocrinology, vol. 140, No. 12, pp. 5828-5840.

Office Action issued May 29, 2008, in U.S. Appl. No. 10/734,640, 19 pages.

Notice of Allowance issued Jun. 13, 2008, in U.S. Appl. 10/734,638, 11 pages.

Ruland et al.; "Influence of Various Penetration Enhancers on the In Vitro Permeation of Amino Acids Across Hairless Mouse Skin"; Internatioinal Journal of Pharmaceutics, vol. 85, No. 1-3, pp. 7-17 (Abstract only).

Friend et al.; "Simply Alkyl Esters as Skin Permeation Enhancers", 1989, Journal of Controlled Release, vol. 9, No. 1 pp. 33-41 (Abstract only).

Santoyo et al.; "Penetration Enhancer Effects on the In Vitro Percutaneous Absorption of Piroxicam Through Rat Skin" 1995; 117: 219-224.

Malet, Catherine et al.; "Effect of 4-hydroxytamoxifen isomerson growth and ultrastructural aspects of normal human breast epithelial (HBE) cells in culture"; Journal of Steroid Biochemistry & Molecular Biology, 82 (2002), pp. 289-296.

Murphy, C.S. et al.; Structure-Function Relationships of Hydroxylated Metabolites of Tamoxifen that Control the Proliferation of Estrogen-Responsive T47D Breast Cancer Cells In Vitro;Molecular Pharmacology 38:737-743 (1990).

* cited by examiner

Figure 1: Mean ± SD Plasma Concentration of 4-Hydroxy Tamoxifen in Healthy Women Following Last Cutaneous Administration (Day 25 of the Second Cycle)

REDUCTION OF BREAST DENSITY WITH 4-HYDROXY TAMOXIFEN

This application claims benefit of priority to U.S. provisional application No. 60/433,958, filed Dec. 18, 2002.

BACKGROUND OF THE INVENTION

The present invention relates to the reduction of breast density with 4-hydroxy tamoxifen (4-OHT). It also relates to improvements in mammographic sensitivity and to reductions in breast cancer risks that attend a reduction in breast density.

The density of a patient's breast tissue depends on the relative proportions of adipose tissue (fat), connective tissue and epithelial tissue. Adipose tissue is the least dense of these three, while connective tissue and epithelial tissue are relatively dense. Thus, breast density is directly proportional with connective and epithelial tissue content. Overall breast composition can range from tissue composed entirely of fat, to tissue predominated by diffuse and/or nodular densities.

The composition of an individual's breast tissue frequently varies over time. For example, breast density inversely correlates with age, postmenopausal status, number of births, and declining body weight. These correlations suggest that histologic changes associated with breast density are under hormonal control. Indeed, women who have dense breasts, as determined by mammography, have higher serum estrogen concentrations than women with less dense breasts. Moreover, estrogen replacement therapy is associated with increased breast density in postmenopausal women (Leung et al., 1997; Saftlas et al., 1987; Jenks et al., 1994; Kaufman et al., 1993).

Dense breast tissue carries at least two important health implications. First, it is one predictor of breast cancer risk (Wolfe, 1976). In fact, studies have shown that high mammographic breast density indicates a 4- to 6-fold increased risk of breast cancer (Byrne et al., 1997; Boyd et al., 1992, 1995). The association between breast density and breast cancer risk appears to stem from increased stromal and epithelial cell proliferation in dense breast tissues.

A second important implication of dense breast tissue is that it affects mammographic sensitivity (Kerlikowske et al., 1996; Ma et al., 1992). This is critical because of current widespread reliance on mammography for cancer detection. Less dense breast tissue, which is dominated by adipose tissue, is easy to assess with mammography, while denser breast tissue is more difficult to assess. On a mammogram, denser breast tissue, such as glands and connective tissue, appears white, while fat appears black. Tumors also appear white on a mammogram. Thus, dense, but normal, breast tissue surrounding a tumor can mask the tumor's presence. It has been demonstrated that higher breast density decreases mammography screening effectiveness by increasing the false-negative rate (Fajardo et al., 1988; Kolb et al., 2002). Moreover, dense mammography patterns decrease radiologists' confidence, leading to more false-positive diagnoses also. These false-positive diagnoses expose patients to unnecessary invasive procedures, such as fine needle aspirations and biopsies, causing both distress and additional health costs.

Given the negative implications of dense breast tissue, methods to reduce breast density are of particular interest. Some reduction can be achieved by carefully following specific dietary guidelines. For instance, adoption of a low-fat (mean, 21% of calories), high-carbohydrate (mean of 61% of calories) diet for 2 years has been shown to reduce the area of mammographic density (Boyd et al., 1997). Also, it has been suggested that a diet containing high amounts of soy may reduce breast density. Results from dietary approaches can be highly variable though. Moreover, ensuring patient compliance with strict dietary approaches is difficult at best.

For post-menopausal women on hormone replacement therapy (HRT), discontinuation of the therapy can decrease breast density (Rutter et al., 2001; Harvey et al., 1997). This approach to reducing breast density has obvious drawbacks. First, it can only work for women on hormone replacement therapy. A large population of women with dense breasts are not on hormone replacement therapy, particularly young women. Second, withdrawal from hormone replacement therapy effects broad systemic changes, and deprives women of HRT's therapeutic benefits. Third, and perhaps most importantly, this approach also can mask an existing tumor. Many breast tumors are hormone receptor positive, meaning that they could regress in response to cessation of hormone replacement therapy, but resume growth upon resumption of hormone replacement therapy. Harvey et al., 1996, report such an occurrence, for instance.

Another approach to reducing breast density entails chemically modulating the effect of hormones on breast tissue. One example of this involves administering a hormonal contraceptive that reduces circulating estrogen and progestogen levels (Spicer et al., 1994; Ursin et al., 1998). However, such hormonal contraceptives have broad systemic effects beyond breast tissue.

Another example involves administering the cancer drug tamoxifen, which has shown some promise for reducing breast density. Tamoxifen's effects on the breast are primarily anti-estrogenic, and mammographic patterns of density appear to be altered by oral tamoxifen. For example, studies have demonstrated a significant change toward a less dense mammographic pattern in the contralateral breasts of post-menopausal breast cancer patients treated with 20 mg/day tamoxifen (Atkinson et al., 1999; Brisson et al., 2000). More dramatic reductions occur in premenopausal patients, who tend to have more dense breasts (Son et al., 1999). Son et al. observed decreased breast parenchyma in 59.8% of women treated with 20 mg/day of tamoxifen after surgery for breast cancer. In premenopausal women, Son found an 87% decrease, compared to only 36% of patients who had not received tamoxifen, and only 10% of healthy control subjects.

Tamoxifen has significant drawbacks in this context. Its action potentially impacts on every estrogen receptor in the body, and, as both an agonist and antagonist, tamoxifen provokes a wide range of systemic effects. These effects increase the risk of endometrial cancer, endometrial hyperplasia and polyps, deep vein thrombosis and pulmonary embolism, changes in liver enzyme levels, and ocular disturbances, including cataracts. Additionally, patients treated with oral tamoxifen reported having hot flashes, vaginal discharge, depression, amenorrhea, and nausea (Fentiman 1986; Fentiman 1988; Fentiman 1989; Ibis 2002).

Thus, an effective approach to reducing breast density would offer significant benefit if it also provoked few systemic side effects.

SUMMARY OF THE INVENTION

The present invention contemplates reducing breast density by administering 4-hydroxy tamoxifen. This treatment approach, preferably implemented topically, improves mammographic sensitivity and reduces the risk of breast cancer. It offers several advantages over other methods for reducing breast density, such as (1) fewer systemic side effects, (2) a better safety profile, and (3) easy patient compliance.

In performing the inventive method, 4-hydroxy tamoxifen may be administered by any means that delivers it to estrogen receptors in vivo. As noted, it is preferable that the administration be done percutaneously (topically), to avoid the first-pass effect and related liver metabolism of the 4-hydroxy tamoxifen. For percutaneous administration, 4-hydroxy tamoxifen may be applied to any skin surface. Application to the breasts is advantageous because 4-hydroxy tamoxifen tends to concentrate in local subcutaneous tissues with estrogen receptors when administered percutaneously.

A broad range of topical formulations are suitable for performing the invention, but hydroalcoholic solutions and hydroalcoholic gels are preferred. The concentration of 4-hydroxy tamoxifen in these formulations may vary, but a dose should result in local 4-hydroxy tamoxifen concentrations that effectively oppose estrogenic driven effects.

DETAILED DESCRIPTION OF THE PREFERRED EMBODIMENTS

As noted, an important aspect of the present invention resides in the discovery that 4-hydroxy tamoxifen effectively reduces breast density, particularly when administered percutaneously. Moreover, it has been discovered that 4-hydroxy tamoxifen provokes fewer unwanted side effects than do other methods for reducing breast density.

Dense breast tissue is easily recognized by mammography. It appears white, whereas non-dense tissue appears dark. Dense breast tissue may be diffuse throughout the breast, or may be nodular. The American College of Radiology (ARC) has developed a system for classifying breast composition, based on density. Four categories exist in the system:

Class I Class I breasts are almost entirely fatty. Mammography is very effective for this class, and is sensitive to even small tumors. Breast cancer risks are smaller for patients with such breasts.

Class II Class II breasts contain scattered fibroglandular tissue. A minor decrease in mammographic sensitivity results in slightly higher risks for this class.

Class III Class III breasts contain heterogenously dense tissue. There is a moderate decrease in mammographic sensitivity for this class, and more elevated breast cancer risks.

Class IV Class IV breasts contain extremely dense tissue. There is a marked decrease in mammographic sensitivity and a higher risk for breast cancer in this class.

The present invention is useful for reducing densities in all radiological classes. Preferably, it is applied to treating breasts in classes II-IV, and more preferably to treating breasts in classes III-IV.

The compound 4-hydroxy tamoxifen, or 1-[4-(2-N-dimethylaminoethoxy)phenyl]-1-(4-hydroxyphenyl)-2-phenyl-but-1-(Z)-ene, constitutes an active metabolite of the well characterized anti-estrogen compound, tamoxifen. Both cis and trans isomers exist, either of which, alone or in combination, are useful according to the present invention. The trans isomer, however, is preferred.

4-Hydroxy tamoxifen acts as a selective estrogen receptor modulator (SERM) that exhibits tissue-specificity for estrogen receptive tissues. In breast tissue, it functions as an estrogen antagonist. Studies have shown that 4-hydroxy tamoxifen can regulate the transcriptional activity of estrogen-related receptors, which may contribute to its tissue-specific activity. In vitro, 4-hydroxy tamoxifen exhibits more potency than tamoxifen, as measured by binding affinity to estrogen receptors, or ERs, and a binding affinity similar to estradiol for estrogen receptors (Robertson et al., 1982; Kuiper et al., 1997). Trans 4-hydroxy tamoxifen inhibits the growth in culture of normal human epithelial breast cells 100 fold more than trans-tamoxifen (Malet et al., 1988).

Although 4-hydroxy tamoxifen is a tamoxifen metabolite, its usefulness for reducing breast density is not presaged by previous experience with tamoxifen itself. Tamoxifen is extensively metabolized by cytochrome P-450 in humans. Thus, its action in vivo is the net result of individual actions by the parent compound and its metabolite compounds competing for the occupation of receptors within target tissues. For example, see Jordan, 1982. Each of these compounds manifests different and unpredictable biological activities in different cells, determined in part by each compound's individual effect on estrogen receptor conformation. That is, estrogen receptor binding of each compound generates a unique receptor-ligand conformation that recruits different cofactors, and results in varying pharmacologies for the different compounds (Wijayaratne et al., 1999; Giambiagi et al., 1988).

Several examples of these varying effects have been documented. For instance, tamoxifen but not 4-hydroxy tamoxifen is a potent rat liver carcinogen. (Carthew et al., 2001; Sauvez et al., 1999). Additionally, tamoxifen but not 4-hydroxy tamoxifen initiates apoptosis in p53(−) normal human mammary epithelial cells (Dietze et al., 2001). By contrast, 4-hydroxy tamoxifen exhibits a significant inhibitory effect on estrone sulphatase activity in mammary cancer cell lines, while tamoxifen has little or no effect in this regard (Chetrite et al., 1993).

Methods for preparing 4-hydroxy tamoxifen are well known. For example, U.S. Pat. No. 4,919,937 to Mauvais-Jarvis et al. describes a synthesis derived from Robertson and Katzenellenbogen, 1982. That synthesis occurs in several stages:

Stage 1—Reaction between 4-(β-dimethylaminoethoxy)-α-ethyldeoxybenzoin and p-(2-tetrahydropyranyloxy) phenylmagnesium bromide;

Stage 2—Separately from stage 1, formation of 1-(4-hydroxyphenyl)-2-phenyl-1-butanone by hydroxylation of 1,2-diphenyl-1-butanone;

Stage 3—Reaction between the products of stages 1 and 2 to form 1-(4-dimethylaminoethoxyphenyl)-1-[p-2-tetrahydropyranyloxy)phenyl]-2-phenylbutan-1-ol;

Stage 4—Dehydration with methanol/hydrochloric acid produces 1-[p-(β-dimethylaminoethoxy)phenyl]-trans-1-(p-hydroxyphenyl)-2-pheny-1-but-1-ene=4-OH-tamoxifen, a mixture of cis and trans isomers;

Stage 5—Separation of the cis and trans isomers by chromatography and crystallization to constant specific activity.

According to the present invention, 4-hydroxy tamoxifen may be administered in any dosage form and via any system that delivers the active compound to estrogen receptors in vivo, preferably to breast estrogen receptors. Preferably, the 4-hydroxy tamoxifen is delivered by "percutaneous administration," a phrase that denotes any mode of delivering a drug from the surface of a patient's skin, through the stratum corneum, epidermis, and dermis layers, and into the microcirculation. This is typically accomplished by diffusion down a concentration gradient. The diffusion may occur via intracellular penetration (through the cells), intercellular penetration (between the cells), transappendageal penetration, (through the hair follicles, sweat, and sebaceous glands), or any combination of these.

Percutaneous administration of 4-hydroxy tamoxifen offers several advantages. First, it avoids the hepatic metabolism that occurs subsequent to oral administration (Mauvais-Jarvis et al., 1986). Second, percutaneous administration significantly reduces systemic drug exposure, and the attendant risks from non-specifically activating estrogen receptors throughout the body; this, because topical 4-hydroxy tamoxifen is absorbed primarily into local tissues. In particular, when 4-hydroxy tamoxifen is percutaneously applied to breasts, high concentrations accumulate in the breast tissue, presumably due to many estrogen receptors therein, without creating a high plasma concentration (Mauvais-Jarvis et al., supra). Pursuant to the present invention, therefore, 4-hydroxy tamoxifen may be applied to any skin surface, but preferably to one or both breasts.

Although the invention is not constrained to any particular theory, clinically significant side effects of anti-estrogen agents occur when the agents displace estradiol in non-target tissues. Because 4-hydroxy tamoxifen and estradiol have similar binding affinities for estrogen receptors, a competition between them for receptor binding would be approximately equal when the concentration of each compound approximates that of the other. If the 4-hydroxy tamoxifen concentration exceeds the estradiol concentration, the former will be bound preferentially to the estrogen receptors, and vice versa.

Accordingly, doses of 4-hydroxy tamoxifen that result in plasma concentrations less than about 80 pg/mL, or the mean estradiol concentration in normal premenopausal women, are preferred. More preferably, doses of 4-hydroxy tamoxifen will result in plasma concentrations less than about 50 pg/mL. The daily doses to be administered can initially be estimated based upon the absorption coefficients of 4-hydroxy tamoxifen, the breast tissue concentration that is desired, and the plasma concentration that should not be exceeded. Of course, the initial dose may be optimized in each patient, depending on individual responses.

As noted above, by targeting 4-hydroxy tamoxifen to breast tissue, high concentrations can be achieved in that tissue without simultaneously raising 4-hydroxy tamoxifen plasma levels to a point where significant systemic competition for estradiol receptors occurs. At a percutaneous dose of 2 mg/day (1 mg/breast/day), 4-hydroxy tamoxifen concentration in breast tissue exceeds normal estradiol concentrations in breast tissue by a factor of 4 (Barrat et al., 1990; Pujol et al., supra). Moreover, 4-hydroxy tamoxifen applied in this manner reaches concentrations in breast tissue that are an order of magnitude higher than concentrations in plasma, i.e., 10:1. By contrast, the breast tissue to plasma ratio of 4-hydroxy tamoxifen following oral administration of tamoxifen is about 5:1.

In a percutaneous formulation, doses on the order of 0.5 mg/day to 3 mg/day (0.25-1.5 mg/breast/day) should achieve the desired result, with doses of about 1.0 mg/day, 1.5 mg/day and 2.0 mg/day (0.5-1.0 mg/breast/day) being preferred.

Percutaneous administration can be accomplished mainly in two different ways: (i) by mixing a therapeutically active compound or its non-toxic pharmaceutically acceptable salt with suitable pharmaceutical carriers and, optionally, penetration enhancers to form ointments, emulsions, lotions, solutions, creams, gels or the like, where an amount of said preparation is applied onto a certain area of the skin, or (ii) by incorporating the therapeutically active substance into patches or transdermal delivery systems according to known technology.

The effectiveness of percutaneous drug administration depends on many factors, including drug concentration, surface area of application, time and duration of application, skin hydration, physicochemical properties of the drug, and partitioning of the drug between the formulation and the skin. Drug formulations intended for percutaneous use take advantage of these factors to achieve optimal delivery. Such formulations often contain penetration enhancers that improve percutaneous absorption by reducing the resistance of the stratum corneum by reversibly altering its physiochemical properties, changing hydration in the stratum corneum, acting as co-solvent, or changing the organization of lipids and proteins in the intercellular spaces. Such enhancers of percutaneous absorption include surfactants, DMSO, alcohol, acetone, propyleneglycol, polyethylene glycol, fatty acids, fatty alcohols and related molecules, pyrrolidones, urea, and essential oils. In addition to chemical enhancers, physical methods can increase percutaneous absorption. For example, occlusive bandages induce hydration of the skin. Other physical methods include iontophoresis and sonophoresis, which use electrical fields and high-frequency ultrasound, respectively, to enhance absorption of drugs that are poorly absorbed due to their size and ionic characteristics.

The many factors and methods relating to percutaneous drug delivery are reviewed in REMINGTON: THE SCIENCE AND PRACTICE OF PHARMACY, Alfonso R. Gennaro (Lippincott Williams & Wilkins, 2000), at pages 836-58, and in PERCUTANEOUS ABSORPTION: DRUGS COSMETICS MECHANISMS METHODOLOGY, Bronaugh and Maibach (Marcel Dekker, 1999). As these publications evidence, those in the pharmaceutical field can manipulate the various factors and methods to achieve efficacious percutaneous delivery.

4-Hydroxy tamoxifen is a large and very lipophilic molecule; hence, without assistance from penetration enhancers it poorly penetrates the skin. Accordingly, formulations of 4-hydroxy tamoxifen used in the present invention preferably contain one or more penetration enhancers. Alcohols are preferred enhancers because 4-hydroxy tamoxifen is soluble in alcohol. Isopropyl myristate also is a preferred enhancer.

For percutaneous administration, 4-Hydroxy tamoxifen may be delivered in an ointment, cream, gel, emulsion (lotion), powder, oil or similar formulation. To this end, the formulation may comprise customary excipient additives, including vegetable oils such as almond oil, olive oil, peach kernel oil, groundnut oil, castor oil and the like, animal oils, DMSO, fat and fat-like substances, lanolin lipoids, phosphatides, hydrocarbons such as paraffins, petroleum jelly, waxes, detergent emulsifying agents, lecithin, alcohols, carotin, glycerol, glycerol ethers, glycols, glycol ethers, polyethylene glycol, polypropylene glycol, non-volatile fatty alcohols, acids, esters, volatile alcoholic compounds, urea, talc, cellulose derivatives, and preservatives.

For practicing the present invention, preferred formulations contain 4-hydroxy tamoxifen in a hydroalcoholic gel. The amount of 4-hydroxy tamoxifen per 100 grams of gel may range from about 0.001 gram to about 1.0 gram. Preferably, it ranges from about 0.01 gram to about 0.1 gram. Table 1 describes the composition of two highly preferred 4-hydroxy tamoxifen gel formulations.

TABLE 1

Composition of 4-Hydroxy Tamoxifen Gel Formulations

| | Quantity per 100 g of gel | |
|---|---|---|
| Ingredient | 20 mg 4-OHT Gel | 57 mg 4-OHT Gel |
| 4-Hydroxy Tamoxifen | 0.02 g | 0.057 g |
| 95% Ethyl Alcohol, EP | 72 g | 72 g |
| Isopropyl myristate, EP | 1 g | 1 g |
| Hydroxypropylcellulose, EP | 1.5 g | 1.5 g |
| Phosphate Buffer (pH 7, diluted 1:4) | q.s. 100 g | q.s. 100 g |

According to the present invention, 4-hydroxy tamoxifen also may be delivered via a transdermal patch. In one embodiment, the patch comprises a reservoir for the 4-hydroxy tamoxifen formula. The patch may comprise (a) a solution-impermeable backing foil, (b) a layer-like element having a cavity, (c) a microporous or semi-permeable membrane, (d) a self-adhesive layer, and (e) optionally, a removable backing film. The layer-like element having a cavity may be formed by the backing foil and the membrane. Alternatively, the patch may comprise (a) a solution-impermeable backing foil, (b) an open-pored foam, a closed-pore foam, a tissue-like layer or a fibrous web-like layer as reservoir, (c) if the layer according to (b) is not self-adhesive, a self-adhesive layer, and (d) optionally a removable backing film.

Reference to the following, illustrative examples will help to provide a more complete understanding of the invention.

EXAMPLE 1

Demonstration of Percutaneous 4-Hydroxy Tamoxifen Delivery

Four patients with breast cancer received [$^3$H]-4-hydroxy tamoxifen in an alcoholic solution applied directly to the breasts at specified intervals between 12 hours to 7 days prior to surgery to excise diseased tissue. After surgery, both the excised tissue and the normal breast tissue surrounding the tumor contained radioactivity (Kuttenn et al., 1985).

In a follow-up study, 9 of 12 patients scheduled for surgical excision of hormone-dependent breast cancer received trans-[$^3$H]-4-hydroxy tamoxifen (80 μCi) in a 60% alcoholic solution, and 3 patients received trans-[$^3$H]-tamoxifen (80 μCi) for comparison. The patients received [$^3$H]-labeled drug applied directly on the affected breasts at specified intervals ranging from 12 hours to 7 days before surgery to excise diseased tissue. Breast tissue from three regions: the tumor, tissue immediately surrounding the tumor, and normal tissue, was excised and immediately frozen in liquid nitrogen. Additionally, plasma and urine samples were obtained at scheduled intervals and frozen until analysis.

Table 2 shows results from the analyses performed. 4-Hydroxy tamoxifen concentrated predominantly in the cytosolic and nuclear fractions of breast tissue, where estrogen receptors are present. In these intracellular sites, 4-hydroxy tamoxifen remained unmetabolized except for limited isomerization from the trans to the cis form. Retention in the breast lasted approximately 4 days in the 4-hydroxy tamoxifen group, but was shorter and far weaker in the tamoxifen group.

TABLE 2

[$^3$H]-4-Hydroxy Tamoxifen and Metabolites Identified in Breast Tumor Tissue Following Percutaneous Administration of Trans-[$^3$H]-4-Hydroxy Tamoxifen to the Affected Breast

| | % Metabolites in Breast Tissue | | | | |
|---|---|---|---|---|---|
| Metabolites | 12 hr[1] | 24 hr | 36 hr | Day 4 | Day 7 |
| 4-Hydroxy Tamoxifen | 97 | 94 | 78 | 70 | 65 |
| N-Desmethyl-4-Hydroxy Tamoxifen | 2 | 4 | 14 | 20 | 16 |
| Bisphenol | 1 | 2 | 3 | 8 | 8 |
| N-Desmethyl tamoxifen | | | <1 | <1 | 3-4 |
| Tamoxifen | | | | <1 | 2 |

[1]Time after administration of trans-[$^3$H]-4-hydroxy tamoxifen

The percentage of radioactivity identified as [$^3$H]-4-hydroxy tamoxifen in breast tissue after percutaneous administration decreased slowly over seven days (from 97% to 65%). During this period a progressive isomerization of the trans isomer into the cis isomer occurred, with similar percentages observed at day 7 (32% and 33%).

The radioactivity in blood due to [$^3$H]-4-hydroxy tamoxifen increased gradually, with a plateau from days 4 to 6. This contrasts with [$^3$H]-tamoxifen, which rapidly appeared in the blood, plateauing at 2 days. At 36 hours following percutaneous [$^3$H]-4-hydroxy tamoxifen administration, only 0.5% of the radioactivity administered showed in the blood.

Marked metabolism of 4-hydroxy tamoxifen occurred in blood, in contrast to the near absence of such metabolism in the breast tissue. At 24 hours after administration, 68% of radioactivity in blood represented 4-hydroxy tamoxifen, 18% represented N-desmethyl-4-hydroxy tamoxifen, and 11% represented bisphenol.

Peak urinary elimination occurred at a later time following percutaneous administration of 4-hydroxy tamoxifen compared to percutaneous tamoxifen. Following application of 4-hydroxy tamoxifen, a progressive increase of metabolites, mostly N-desmethyl-4-hydroxy tamoxifen and bisphenol, was observed in the urine.

This example demonstrates that percutaneous application of 4-hydroxy tamoxifen to the breasts results in a substantial and lasting local tissue concentration of the drug, with minimal metabolism, stable and very low plasma concentrations, and slow elimination via the urine.

EXAMPLE 2

Demonstration of the Pharmacokinetics and Pharmacodynamics of Percutaneously Administered 4-OH-Tamoxifen Compared to 20 mg of Oral Tamoxifen This study compared the tissue and plasma concentrations of 4-hydroxy tamoxifen after percutaneous administration via a hydroalcoholic gel with tissue and plasma concentrations of 4-hydroxy tamoxifen after oral administration of tamoxifen. (Pujol et al.).

Thirty-one patients scheduled for breast cancer surgery were randomly assigned to 1 of 5 groups. They received treatment with either oral tamoxifen or percutaneous 4-hydroxy tamoxifen as outlined in Table 3. Treatment was daily and lasted for 3-4 weeks prior to surgery. The study evaluated three different doses of 4-hydroxy tamoxifen (0.5, 1, or 2 mg/day) and two areas of application (either to both breasts or to a large surface of skin including arms, forearms, and shoulders). One group of patients received 20 mg/day (10 mg b.i.d.) of oral tamoxifen (Nolvaldex®).

TABLE 3

Treatment Groups

| Group | N | Drug | Application Site | Dose mg/breast/day | Total Daily Dose (mg/day) |
|---|---|---|---|---|---|
| 1 | 6 | PO tamoxifen | — | — | 20[a] |
| 2 | 6 | 4-OHT gel | both breasts | 0.25 | 0.5 |
| 3 | 5 | 4-OHT gel | both breasts | 0.50 | 1 |
| 4 | 5 | 4-OHT gel | arms, forearms, and shoulders | — | 1 |
| 5 | 6 | 4-OHT gel | arms, forearms, and shoulders | — | 2[b] |

[a] 10 mg b.i.d.
[b] divided into 2 daily applications; 1 mg in the morning and 1 mg in the evening The 4-hydroxy tamoxifen gel (20 mg of 4-hydroxy tamoxifen/100 g of hydroalcholic gel; Besins-Iscovesco Laboratories) was packaged in a pressurized dose-metering pump that delivered 1.25 g of gel/metered dose (i.e., 0.25 mg of 4-hydroxy tamoxifen/dose).

During surgery, two samples (1 cm$^3$ each) of breast tissue were excised, one tumoral and the other macroscopically normal. They were immediately frozen in liquid nitrogen until assayed. Blood samples were obtained on the day of and the day prior to surgery. All tissue and plasma samples were analyzed for 4-hydroxy tamoxifen concentration by gas chromatograph/mass spectrometry (GC-MS).

Pre and post-treatment blood samples were assayed for complete blood counts (CBC), bilirubin, serum glutamic-pyruvic transaminase (SGPT), serum glutamic-oxaloacetic transaminase (SGOT), alkaline phosphatase, creatinine, estradiol, follicle-stimulating hormone (FSH), lutenizing hormone (LH), sex hormone-binding globulin (SHBG), cholesterol, high-density lipoprotein (HDL), low-density lipoprotein (LDL), triglycerides, fibrinogen, and anti-thrombin III.

Table 4 below summarizes the concentration of 4-hydroxy tamoxifen found in breast tissue and plasma. Normal and tumor breast tissues contained similar concentrations of 4-hydroxy tamoxifen in all five treatment groups. 4-hydroxy tamoxifen concentrated at higher amounts in breast tissue when the gel was applied directly to the breasts, rather than to other large skin surfaces.

Side effects did not pose a significant problem. Cutaneous treatment did not cause any local irritation. One woman in Group 2 (0.5 mg/day of 4-hydroxy tamoxifen gel) reported dizzy spells, cystitis, and mild vaginitis occurring on the seventh day of treatment. One woman in Group 1 (oral tamoxifen) reported hot flashes and mild vaginitis on the fifth day of treatment.

No differences existed between the pre- and post treatment blood samples for any of the hematology or serum chemistry evaluations in the patients who received 4-hydroxy tamoxifen gel. However, a statistically significant decrease in antithrombin III and fibrinogen and a statistically significant increase in platelet and lymphocyte counts were observed in the oral tamoxifen group, consistent with the biologic effects of this drug observed in other studies.

TABLE 4

Concentrations of 4-hydroxy tamoxifen

Mean ± SD 4-hydroxy tamoxifen (Range)

| Group | N | Plasma Concentrations (pg/mL) Day Pre-Surgery | Day of Surgery | Normal Tissue (pg/g) | Tumor (pg/g) |
|---|---|---|---|---|---|
| 1 | 6 | 2326 ± 585 (1371-2959)[a] | 2317 ± 1098 (881-4176) | 10215 ± 2151 (5873-11511) | 12453 ± 3751 (9568-18904)[a] |
| 2 | 6 | 0 (0-0)[a] | 17 ± 27 (0[c]-61) | 353 ± 513 (0[d]-1317) | 1447 ± 2673 (0[f]-6889) |
| 3 | 5 | 164 ± 131 (29-279)[b] | 62 ± 71 (28-190) | 1112 ± 1125 (197-2979) | 1877 ± 2472 (345-6211) |
| 4 | 5 | 94 ± 76 (35-201)[b] | 13 ± 29 (0[c]-65) | 140 ± 130 (0[e]-270) | 552 ± 357 (271-1150) |
| 5 | 6 | 78 ± 138 (0[e]-284)[b] | 73 ± 114 (0[e]-244) | 992 ± 2195 (0[d]-5462) | 224 ± 312 (0[d]-799) |

[a] n = 5
[b] n = 4
[c] Four patients had undetectable levels of 4-hydroxy tamoxifen (LOQ = 20 pg/ml).
[d] Three patients had undetectable levels of 4-hydroxy tamoxifen.
[e] 2 patients had undetectable levels of 4-hydroxy tamoxifen
[f] 1 patient had undetectable levels of 4-hydroxy tamoxifen

EXAMPLE 3

Demonstration of Tolerance and Pharmacokinetics of Percutaneously Administered 4-OH-Tamoxifen in Healthy Women This study demonstrates the tolerance and pharmacokinetics of topically applied 4-hydroxy tamoxifen gel in healthy premenopausal women, aged 18-45. Each participant applied the gel daily for the duration of two menstrual cycles.

Three doses and two gel concentrations were tested, as summarized in Table 5. For Groups A-C, the gel, containing 20 mg of 4-hydroxy tamoxifen/100 g, was dispensed from a pressurized dose-metering pump that delivered 0.25 mg of 4-hydroxy tamoxifen/dose. The study of Group C was suspended because the quantity of gel was too large to be applied to a single breast. Groups D and E received a more concentrated gel that contained almost 3 times as much 4-hydroxy tamoxifen: 57 mg of 4-hydroxy tamoxifen/100 g, or 50 mg of 4-hydroxy tamoxifen/100 mL of gel. This more concentrated gel also was delivered by a dose-metering pump that supplied 0.25 mg of 4-hydroxy tamoxifen/dose.

TABLE 5

Treatment Groups

| Group | N | Dose (mg/day) | Gel Concentration (mg of 4-OHT/g of gel) | Treatment |
|---|---|---|---|---|
| A | 12 | 0.5 | 20 mg/100 g | 1 metered dose/breast/day |
| B | 8 | 1 | 20 mg/100 g | 2 metered doses/breast/day |
| C | 2 | 2 | 20 mg/100 g | study was interrupted |
| D | 12 | 1 | 57 mg/100 g | 2 metered doses/breast/day |
| E | 12 | 2 | 57 mg/100 g | 4 metered doses/breast/day |

At the end of a menstrual cycle, each patient received a single dose, after which serial blood samples were collected at 0, 0.5, 1, 1.5, 2, 3, 4, 6, 12, 18, 24, 36, 48, and 72 hours.

On the first day of the following menstruation, treatment, which consisted of daily application of the gel over two menstrual cycles, began. Blood samples were collected 24 hours following the morning application of gel on days 7, 20 and 25 of the first and second cycles. On the last day of administration, day 25 of the second menstrual cycle, serial blood samples were collected prior to application and at 0.5, 1, 1.5, 2, 3, 4, 6, 12, 18, 24, 36, 48, and 72 hours after application of the gel. The samples were analyzed for 4-hydroxy tamoxifen, estradiol, progesterone, FSH and LH.

Plasma concentrations of 4-hydroxy tamoxifen remained detectable 72 hours after the last gel application. Therefore, to ensure that data points were obtained until 4-hydroxy tamoxifen became undetectable in the blood, additional blood samples were collected from some participants at intervals up to 92 days following the last application of gel.

Table 6 displays the mean ± standard deviation (SD) plasma concentrations of 4-hydroxy tamoxifen, with ranges in parentheses. A single 0.5 mg dose did not produce detectable plasma concentrations of 4-hydroxy tamoxifen, but 6 of 12 patients had detectable plasma concentrations (>5 pg/mL) after a single dose of 1 mg.

TABLE 6

Mean ± SD Plasma Concentrations of 4-hydroxy tamoxifen in Healthy Women Following Daily Cutaneous Administration for Two Menstrual Cycles

| Cycle | Day | Time after Application (hr) | Mean ± SD (Range is indicated in parenthesis) in pg/mL | | | |
|---|---|---|---|---|---|---|
| | | | 0.5 mg/day (n = 12)[1] | 1 mg/day (n = 8)[1] | 1 mg/day (n = 12)[2] | 2 mg/day (n = 12)[2] |
| First | 1 | 0 | (0-17.2) | (0-13.9) | (0-9.5) | (0-0) |
| | 7 | 24 | 6.4 ± 5.6 (<LOQ-16.8) | 15.2 ± 9.7 (<LOQ-26.8) | 14.4 ± 13.1 (<LOQ-37.9) | 26.9 ± 18.2 (8.9-71.3) |
| | 20 | 24 | 13.6 ± 7.9 (<LOQ-25.9) | 17.3 ± 9.5 (<LOQ-29.8) | 18.1 ± 15.8 (<LOQ-44.5) | 44.0 ± 29.2 (10.5-117.5) |
| | 25 | 24 | 23.9 ± 23.4 (<LOQ-73.1) | 15.5 ± 6.6 (6.4-25.0) | 19.8 ± 16.2 (6.2-57.0) | 45.4 ± 31.0 (17.9-120.1) |
| Second | 7 | 24 | 25.2 ± 16.1 (6.5-61.7) | 17.4 ± 11.2 (5.7-39.6) | 22.2 ± 16.4 (9.0-64.4) | 42.2 ± 24.8 (18.2-98.0) |
| | 20 | 24 | 15.7 ± 14.0 (<LOQ-52.3) | 14.8 ± 6.5 (5.4-24.8) | 24.4 ± 20.1 (<LOQ-65.4) | 38.9 ± 27.1 (18.7-119.7) |
| | 25 | 0[3] | 10.8 ± 9.9 (<LOQ-36.4) | 15.7 ± 17.1 (<LOQ-56.4) | 27.2 ± 20.8 (8.0-72.1) | 43.2 ± 27.7 (16.9-120.3) |
| | | 0.5 | 10.9 ± 7.4 (<LOQ-26.0) | 13.5 ± 9.1 (<LOQ-27.7) | 25.9 ± 18.7 (8.7-69.2) | 44.5 ± 29.9 (13.6-124.5) |
| | | 1 | 10.4 ± 7.8 (<LOQ-26.7) | 10.8 ± 6.6 (<LOQ-23.8) | 28.7 ± 19.5 (8.8 ± 69.2) | 40.5 ± 25.1 (14.2-106.7) |
| | | 1.5 | 9.0 ± 8.2 (<LOQ-25.1) | 11.8 ± 8.0 (<LOQ-23.6) | 25.6 ± 17.8 (7.5-67.0) | 36.8 ± 21.1 (15.9-90.0) |
| | | 2 | 11.8 ± 9.5 (<LOQ-26.9) | 10.7 ± 6.9 (<LOQ-24.7) | 25.1 ± 18.0 (6.9-67.3) | 36.8 ± 21.6 (13.0-83.7) |
| | | 3 | 10.0 ± 7.9 (<LOQ-23.1) | 11.4 ± 7.9 (<LOQ-28.1) | 24.8 ± 20.5 (9.0-69.9) | 36.1 ± 20.6 (11.9-89.4) |
| | | 4 | 9.2 ± 8.3 (<LOQ-25.3) | 11.2 ± 7.3 (<LOQ-25.7) | 26.8 ± 23.3 (6.4-78.1) | 38.1 ± 21.2 (16.5-92.0) |
| | | 6 | 11.4 ± 8.5 (<LOQ-26.6) | 10.7 ± 6.4 (<LOQ-22.8) | 25.0 ± 18.2 (9.0-65.3) | 41.0 ± 29.1 (14.0-123.8) |
| | | 12 | 11.0 ± 9.7 (<LOQ-29.1) | 11.8 ± 7.8 (<LOQ-28.1) | 28.3 ± 22.9 (6.4-74.6) | 45.1 ± 30.6 (18.7-126.8) |
| | | 18 | 9.7 ± 8.8 (<LOQ-24.9) | 12.2 ± 8.3 (<LOQ-29.6) | 23.4 ± 17.4 (8.1-57.9) | 39.8 ± 25.5 (16.0-107.3) |
| | 26 | 24 | 12.4 ± 9.4 (<LOQ-34.4) | 18.6 ± 14.2 (<LOQ-40.1) | 26.0 ± 19.6 (8.9-61.9) | 44.0 ± 33.0 (15.8-132.5) |
| | | 36 | 10.9 ± 6.9 (5.0-25.8) | 13.4 ± 7.5 (<LOQ-25.4) | 25.7 ± 18.4 (8.8-61.3) | 42.1 ± 31.5 (15.1-129.3) |
| | 27 | 48 | 12.1 ± 6.5 (4.8-26.6) | 12.5 ± 6.0 (<LOQ-19.6) | 22.0 ± 16.0 (5.6-50.2) | 38.1 ± 25.3 (17.5-110.0) |

TABLE 6-continued

Mean ± SD Plasma Concentrations of 4-hydroxy tamoxifen in
Healthy Women Following Daily Cutaneous Administration for Two
Menstrual Cycles

| | | Time after | Mean ± SD (Range is indicated in parenthesis) in pg/mL | | | |
|---|---|---|---|---|---|---|
| Cycle | Day | Application (hr) | 0.5 mg/day $(n = 12)^1$ | 1 mg/day $(n = 8)^1$ | 1 mg/day $(n = 12)^2$ | 2 mg/day $(n = 12)^2$ |
| | 28 | 72 | 9.9 ± 7.1 (<LOQ-22.3) | 9.9 ± 5.8 (<LOQ-19.6) | 18.9 ± 12.4 (5.6-37.8) | 33.2 ± 22.2 (17.7-98.0) |
| | | +5 days | — | 5.8 ± 5.2 (<LOQ-12.4) | 11.4 ± 8.2 (<LOQ-25.8) | 20.4 ± 17.3 (9.1-71.6) |
| | | +8 days | <LOQ | (<LOQ-17.4) | (0-14.8) | 10.8 ± 13.4 (<LOQ-52.0) |
| | | +12 days | (maximum 9.09) | (<LOQ-7.0) | (0-<LOQ) | (0-30.4) |
| | | +20 days | 0 | <LOQ | (0-<LOQ) | (0-<LOQ) |

LOQ = limit of quantification (<5 pg/mL)
[1]Gel concentration was 20 mg of 4-hydroxy tamoxifen per 100 g of gel.
[2]Gel concentration was 57 mg of 4-hydroxy tamoxifen per 100 g of gel.
[3]Timepoint 0 is 24 hours after the application on Day 24 and prior to the final application on Day 25.

Figure 1:
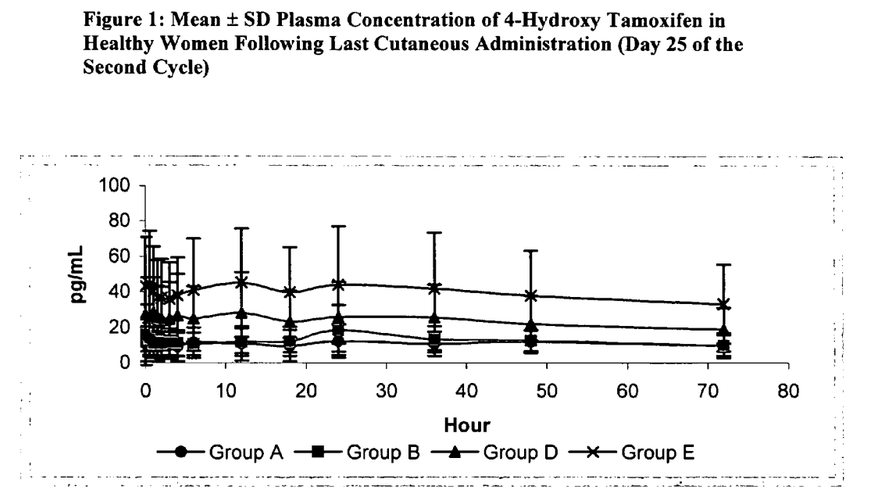
FIG. 1 illustrates the mean plasma concentration of 4-hydroxy tamoxifen in healthy women following cutaneous administration.

FIG. 1 shows a plasma concentration-time curve, following the last administration on day 25 of the second menstrual cycle. Table 7 shows mean pharmacokinetic parameters that relate to the last administration, on day 25 of the second menstrual cycle.

TABLE 7

Mean Pharmacokinetic Parameters of
4-hydroxy tamoxifen in Healthy
Women Following the Last Administration

| | Mean ± SD (Range is indicated in parenthesis) | | | |
|---|---|---|---|---|
| Parameter | 0.5 mg/day $(n = 12)^a$ | 1 mg/day $(n = 8)^a$ | 1 mg/day $(n = 12)^b$ | 2 mg/day $(n = 12)^b$ |
| $C_{max}$ (pg/mL) | 17.0 ± 8.5 (7.6-34.4) | 21.0 ± 14.0 (<LOQ-40.1) | 35.1 ± 22.4 (9.9-78.1) | 51.6 ± 31.7 (22.1-132.5) |
| $t_{max}$ (hr) | 40 ± 81 (0.5-288) | 24 ± 18 (0.5-48) | 12.8 ± 14.9 (1-36) | 11.8 ± 12.3 (0.5-36) |
| $t_{1/2}$ (hr) | — | — | (58-118) | (49-101) |
| $AUC_{0-24}$ (pg · hr/mL) | 256.3 ± 205.3 (24.6-651.1) | 300.9 ± 190.8 (0-693.6) | 619 ± 466 (187-1522) | 998 ± 653 (424-2778) |
| $C_{av} = AUC_{0-24}/24$ (pg/mL) | 10.7 ± 8.5 (1.0-27.1) | 12.5 ± 7.9 (0-28.9) | 25.8 ± 19.4 (7.8-63.4) | 41.6 ± 27.2 (17.7-115.8) |
| T(1stC < LOQ) (hr) | — | 274 ± 141 (144-480) | 236 ± 72 (144-384) | 326 ± 97 (192-480) |

[a]Gel concentration was 20 mg of 4-hydroxy tamoxifen per 100 g of gel.
[b]Gel concentration was 57 mg of 4-hydroxy tamoxifen per 100 g of gel.

$AUC_{0-24}$=area under the concentration-time curve for 0-24 hours; $C_{av}$=Calculation of area under the curve over 24 hours ($AUC_{0-24}$) divided by 24 hours; $C_{max}$=maximal concentration in plasma; $t_{1/2}$=half-life; T(1stC<LOQ)=first timepoint at which the plasma concentration was below the limit of quantification; $t_{max}$=time of maximal concentration in plasma.

The data are consistent with a dose response across the three doses tested (0.5, 1, and 2 mg). The more concentrated gel was better absorbed, by approximately double, than the less concentrated gel, based on AUC and $C_{av}$.

Biological tolerance was excellent in all 36 patients. The treatment did not affect FSH, LH, estradiol, or progesterone hormone levels during the menstrual cycles. Moreover, echographic examination of the ovaries at the end of treatment was normal in all patients, showing normal sized developing follicles. One patient developed an allergic reaction to the gel, and 10 reported facial acne.

In summary, this study indicates that the exposure to 4-hydroxy tamoxifen after topical application increases with dose, that plasma concentrations of 4-hydroxy tamoxifen are lower than typical estradiol concentrations (80 pg/mL), and that there is no detectable laboratory or clinical evidence of systemic effects.

EXAMPLE 4

Study to Demonstrate Efficacy for Percutaneous
4-Hydroxy Tamoxifen in Reducing Mammographic
Density of Breast Tissue The primary objective of this study is to demonstrate that 4-hydroxy tamoxifen, when administered percutaneously, effectively reduces the mammographic density of breast tissue.

Women on continuous hormone replacement therapy, and who have moderate or extremely dense breasts, receive either placebo or 4-hydroxy tamoxifen gel. After a period of 4 months, digitized mammography shows a statistically significant decrease in dense area for patients receiving 4-hydroxy tamoxifen gel at doses of 1.5 and 2.0 mg/day.

CITED PUBLICATIONS

Each of the following cited references is incorporated herein in its entirety.

Atkinson, C., R. Warren, S. A. Bingham, and N. E. Day, Mammographic patterns as a predictive biomarker of breast cancer risk: effect of tamoxifen, Cancer Epidemiology, Biomarkers & Prevention, 8: 863-66 (1999).

Barrat, J., B. de Lignieres, L. Marpeau, L. Larue, S. Fournier, K. Nahoul, G. Linares, H. Giorgi, and G. Contesso, Effet in vivo de l'administration locale de progesterone sur l'activite mitotique des galactophores humains, J. Gynecol. Obstet. Biol. Reprod. 19:269-274 (1990) (French).

Boyd, N. F., H. M. Jensen, G. Cooke, and H. Lee-Han, Relationship between mammographic and histological risk factors for breast cancer, JNCI, 84: 1170-79 (1992).

Boyd, N. F., J. W. Byng, R. A. Jong, E. K. Fishell, L. E. Little, A. B. Miller, G. A. Lockwood, D. L. Tritchler, and M. J. Yaffee, Quantitative classification of mammographic densities and breast cancer risk: results from the Canadian national breast screening study, JNCI, 87: 670-75 (1995).

Boyd, N. F., C. Greenberg, G. Lockwood, L. Little, L. Martin, J. Byng, M. Yaffe, and D. Tritchler, Effects at two years of a low-fat, high-carbohydrate diet on radiologic features of the breast: results from a randomized trial, JNCI, 89(7): 488-96 (1997).

Brisson, J., B. Brisson, G. Cote, E. Maunsell, S. Berube, and J. Robert, Tamoxifen and mammographic breast densities, Cancer Epidemiology, Biomarkers & Prevention, 9: 911-15 (2000).

Bronaugh and Maibach, Percutaneous Absorption: Drugs Cosmetics Mechanisms Methodology, Marcel Dekker 1999.

Byrne, C., Studying mammographic density: implications for understanding breast cancer, JNCI, 89: 531-33 (1997).

Carthew, P., P. N. Lee, R. E Edwards, R. T. Heydon, B. M. Nolan, E. A. Martin, Cumulative exposure to tamoxifen: DNA adducts and liver cancer in the rat, Arch Toxicol, 75: 375-80 (2001).

Chetrite, G., C. Varin, L. Delalonde, J. R. Pasqualini, Effect of promegestone, tamoxifen, 4-hydroxytamoxifen and ICT 164,384 on the oestrone sulphatase activity of human breast cancer cells, Anticancer Res, 13(4) 931-4 (Juyl-August 1993).

Dietze, E. C., L. E. Caldwell, S. L. Grupin, M. Mancini, and V. L. Seewald, Tamoxifen, but not 4-hydroxytamoxifen initiates apoptosis in p53(−) normal human mammary epithelial cells by inducing mitochondrial depolarization, J. Biol. Chem., 276(7): 5384-94 (Feb. 16, 2001).

Fajardo, L. L., B. J. Hillman, and C. Frey, Correlation between breast parenchymal patterns and mammographer's certainty of diagnosis, Invest. Radiol., 23: 505-8 (1988).

Fentiman, I. S., Tamoxifen and mastalgia. An emerging indication, Drugs 32: 477-80 (1986).

Fentiman, I. S., M. Caleffi, H. Hamed, and M. A. Chaudary, Dosage and duration of tamoxifen treatment for mastalgia: a controlled trial, British Journal of Surgery 75: 845-46 (1988).

Fentiman, I. S., M. Caleffi, H. Hamed, and M. A. Chaudary, Studies of tamoxifen in women with mastalgia, British Journal of Clinical Practice, Supplement 68, 43(11): 34-36 (1989))

Giambiagi, N. and J. R. Pasqualini, Immunological differences between the estradiol-, tamoxifen and 4-hydroxytamoxifen estrogen receptor complexes detected by two monoclonal antibodies, J. Steroid Biochem, 30(1-6): 213-7 (1988).

Harvey, S. C., P. J. DiPiro, and J. E. Meyer, Marked regression of a nonpalpable breast cancer after cessation of hormone replacement therapy, AJR Am. J. Roentgenology, 167: 394-95 (1996).

Harvey, J. A., J. V. Pinkerton, and C. R. Herman, Short-term cessation of hormone replacement therapy and improvement of mammographic specificity, JNCI, 89(21): 1623-25 (1997).

IBIS Investigators, First results from the International Breast Cancer Intervention Study (IBIS-I): a randomised prevention trial, Lancet, 360(9336): 817-24 (2002).

Jenks, S., Dense breast tissues may hold increased cancer risk for some, JNCI, 86: 578-80 (1994).

Jordan, V. C., Metabolites of tamoxifen in animals and man: identification, pharmacology, and significance, Breast Cancer Res. Treat., 2(2) 123-38 (1982).

Kerlikowske, J., D. Grady, J. Barclay, E. A. Sickles, and V. Ernster, effect of age, breast density, and family history on the sensitivity of first screening mammography, JAMA, 276: 33-40 (1996).

Kaufman, Z, W. I. H. Garstin, R. Hayes, M. J. Mitchell, and M. Baum, The mammographic parenchymal patterns of women on hormonal replacement therapy, Clin. Radiol., 43: 389-92 (1991).

Kolb, T. M., J. Lichy and J. H. Newhouse, Comparison of the performance of screening mammography, physical examination, and breast ultrasound and evaluation of factors that influence them: an analysis of 27,825 patient evaluations, Radiology, 225: 165-75 (2002).

Kuiper, G. G. J. M., B. Carlsson, K. Grandien, E. Enmark, J. Heggblad, S. Nilsson, J. Gustafsson, Comparison of the ligand binding specificity and transcript tissue distribution of estrogen receptors α and β, Endocrinology, 138:863-870 (1997).

Kuttenn, F. and P. Mauvais-Jarvis, Intratumoral levels and metabolism of 4-hydroxytamoxifen after percutaneous administration at the breast level, C.R. Acad. Sci. III. 300: 457-462 (1985) (French).

Leung, W. F. Goldberg, B. Zee, and E. Sterns, Mammographic density in women on postmenopausal hormone replacement therapy, Surgery, 122(4): 669-672 (1997).

Ma, L., E. Fishell, B. Wright, W. Hanna, S. Allan, and N. F. Boyd, Case-control study of factors associated with failure to detect breast cancer by mammography, JNCI, 84: 781-5 (1992).

Malet C, A. Gompel, P. Spritzer, N Bricourt, NH Yaneva, I. Mowszowicz, F. Kutten and P Mauvais Jarvis, Tamoxifen and hydroxytamoxifen isomers versus estradiol effects on normal human breast cells in culture, Cancer Research, 48: 7193-7199 (1988).

Mauvais-Jarvis, P., N. Baudot, D. Castaigne, P. Banzet, and F. Kuttenn, Trans-4-hydroxytamoxifen concentration and metabolism after local percutaneous administration to human breast, Cancer Research, 46:1521-1525 (1986).

Pujol, H., J. Girault, P. Rouanet, S. Fournier, J. Grenier, J. Simony, J. B. Fourtillan, and J. L. Pujol, Phase 1 study of percutaneous 4-hydroxy-tamoxifen with analyses of 4-hydroxy-tamoxifen concentrations in breast cancer and normal breast tissue, Cancer Chemother. Pharmacol., 36:493-498 (1995).

Remington: The Science and Practice of Pharmacy, Alfonso R. Gennaro, Lippincott Williams & Wilkins, 2000, pp. 836-858.

Robertson and Katzenellenbogen, J. Org. Chem., 47: 2387 (1982).

Robertson, D. W., J. A. Katzenellenbogen, D. J. Long, E. A. Rorke and B. S. Katzenellenbogen, Tamoxifen antiestrogens. A comparison of the activity, pharmacokinetics, and metabolic activation of the cis and trans isomers of tamoxifen, J. Steroid Biochemistry, 16(1):1-13 (1982).

Rutter, C. M., M. T. Mandelson, M. B. Laya, and S. Taplin, Changes in breast density associated with initiation, discontinuation, and continuing use of hormone replacement therapy, JAMA, 285(2): 171-76 (2001).

Saftlas, A. F., and M. Szklo, Mammographic parenchymal patterns and breast cancer risk, Epidemiologic Reviews, 9: 146-74 (1987).

Sauvez, F., D. Salin-Drouin, M. Attia, H. Bertheux, and R. Forster, Cutaneously applied 4-hydroxytamoxien is not carcinogenic in female rats. Carcinogenesis, 20: 843-50 (1999).

Son, H. J., and K. K. Oh, Significance of follow-up mammography in estimating the effect of tamoxifen in breast cancer patients who have undergone surgery, American Journal of Roentgenology, 173: 905-909 (1999).

Spicer, D. V., G. Ursin, Y. Parisky, R. Pearce, J. G. Shoupe, A. Pike, and M. Pike, Changes in mammographic densities induced by a hormonal contraceptive designed to reduce breast cancer risk, JNCI, 86: 431-36 (1994).

Ursin, G., M. Astrahan, M. Salane, Y. Parisky, J. Pearce, J. Daniels, M. Pike, and D. Spicer, The detection of changes in mammographic densities, Cancer Epidemiol. Biomark. Prev., 7: 43-47 (1998).

Wijayaratne, A. L., S. C. Nagel, L. A. Paige, D. J. Christensen, J. D. Norris, D. M. Fowlkes, and D. P. McDonnell, Comparative Analyses of Mechanistic Difference among Antiestrogens, Endocrinology, 140(12): 5828-5840 (1999).

Wolfe, J. N., Risk for breast cancer development determined by mammographic parenchymal pattern, Cancer, 37: 2486-92 (1976).

What is claimed is:

1. A method of reducing breast density, comprising percutaneously administering, to a patient having class III or class IV dense breast composition, a pharmaceutical composition for percutaneous administration comprising 4-hydroxy tamoxifen and isopropyl myristate.

2. A method according to claim 1, wherein said dense breast tissue is diffuse.

3. A method according to claim 1, wherein said dense breast tissue is nodular.

4. A method according to claim 1, wherein said 4-hydroxy tamoxifen is a blend of trans and cis isomers.

5. A method according to claim 1, wherein said 4-hydroxy tamoxifen is a trans isomer.

6. A method according to claim 1, wherein greater than about 0.5 mg/breast of said 4-hydroxy tamoxifen is administered per day.

7. A method according to claim 1, wherein greater than about 0.75 mg/breast of said 4-hydroxy tamoxifen is administered per day.

8. A method according to claim 1, wherein greater than about 1.0 mg/breast of said 4-hydroxy tamoxifen is administered per day.

9. A method according to claim 1, wherein said pharmaceutical composition comprises a hydroalcoholic gel.

10. A method according to claim 9, wherein said hydroalcoholic gel comprises ethyl alcohol, isopropyl myristate, and hydroxypropylcellulose.

11. A method according to claim 1, wherein said pharmaceutical composition comprises an alcoholic solution.

12. A method of improving mammographic sensitivity that comprises performing the method of claim 1, then performing mammography on said patient.

13. A method according to claim 12, wherein said 4-hydroxy tamoxifen is a blend of trans and cis isomers.

14. A method according to claim 12, wherein said 4-hydroxy tamoxifen is a trans isomer.

15. A method according to claim 12, wherein greater than about 0.5 mg/breast of said 4-hydroxy tamoxifen has been administered per day.

16. A method according to claim 12, wherein greater than about 0.75 mg/breast of said 4-hydroxy tamoxifen has been administered per day.

17. A method according to claim 12, wherein greater than about 1.0 mg/breast of said 4-hydroxy tamoxifen has been administered per day.

18. A method according to claim 12, wherein said pharmaceutical composition comprises a hydroalcoholic gel.

19. A method according to claim 18, wherein said hydroalcoholic gel comprises ethyl alcohol, isopropyl myristate, and hydroxypropylcellulose.

20. A method according to claim 9, wherein said pharmaceutical composition comprises 4-hydroxy tamoxifen, ethyl alcohol, isopropyl myristate, hydroxypropylcellulose and phosphate buffer.

21. A method according to claim 9, wherein said pharmaceutical composition comprises from about 0.001 g to about 1.0 g of 4-hydroxy tamoxifen per 100 g gel.

22. A method according to claim 21, wherein said pharmaceutical composition comprises from about 0.01 g to about 0.1 g of 4-hydroxy tamoxifen per 100 g gel.

23. A method according to claim 18, wherein said pharmaceutical composition comprises 4-hydroxy tamoxifen, ethyl alcohol, isopropyl myristate, hydroxypropylcellulose and phosphate buffer.

24. A method according to claim 18, wherein said pharmaceutical composition comprises from about 0.001 g to about 1.0 g of 4-hydroxy tamoxifen per 100 g gel.

25. A method according to claim 24, wherein said pharmaceutical composition comprises from about 0.01 g to about 0.1 g of 4-hydroxy tamoxifen per 100 g gel.

* * * * *